(12) United States Patent
Izhar

(10) Patent No.: US 6,852,911 B1
(45) Date of Patent: Feb. 8, 2005

(54) METHOD OF PRODUCING A MALE STERILE PLANT BY EXOGENIC ALLELISM

(75) Inventor: Shamay Izhar, Rehovot (IL)

(73) Assignee: Fertiseed Ltd., Sitrya (IR)

( * ) Notice: Subject to any disclaimer, the term of this patent is extended or adjusted under 35 U.S.C. 154(b) by 0 days.

(21) Appl. No.: 09/411,863

(22) Filed: Oct. 4, 1999

Related U.S. Application Data

(60) Provisional application No. 60/151,627, filed on Aug. 31, 1999.

(51) Int. Cl.[7] ............................ A01H 5/00; A01H 5/10; C12N 15/82
(52) U.S. Cl. ...................... 800/303; 800/278; 800/288; 800/287; 800/286
(58) Field of Search ................................ 800/278, 303, 800/288, 286, 287, 274, 298; 435/320.1, 468, 469

(56) References Cited

U.S. PATENT DOCUMENTS

| | | | | |
|---|---|---|---|---|
| 5,426,041 A | * | 6/1995 | Fabijanski et al. | 435/172.3 |
| 5,929,307 A | * | 7/1999 | Hodges et al. | 800/303 |
| 6,392,119 B1 | * | 5/2002 | Gutterson et al. | |

OTHER PUBLICATIONS

Stuurman et al, 1996, Plant Mol. Biol. 32:901–913.*
Kilby et al, 1995, Plant J. 8:637–652.*
Sonti et al, 1995, Plant Mol. Biol. 28:1127–1132.*
Kilby et al, 2000, J. Exp. Bot 51:853–863.*
Gidoni et al, 2001, Euphytica 121:145–156.*
Medberry, S. L. et al. "Intra–chromosomal rearrangements generated by Cre–iox site–specific recombination." 1995, Nucleic Acids Research, vol. 23, pp. 485–490.*
Golic, K. G. "Site–Specific Recombination Between Homologous Chromosomes in Drosophila." 1991, Science, vol. 252, pp. 958–961.*
Luo, H. et al. "FLP–mediated recombination for use in hybrid plant production." 2000, The Plant Journal, vol. 23, pp. 423–430.*
Qin, M. et al. "Cre recombinase–mediated site–specific recombination between plant chromosomes." 1994, Proc. Natl. Acad. Sci. USA, vol. 91, pp. 1706–1710.*
Snaith, M. R. et al. "Multiple cloning sites carrying IoxP and FRT recognition sites for the Cre and Flp site–specific recombinases." 1995, Gene, vol. 166, pp. 173–174.*
Vergunst, A. C. et al. "Site–specific integration of Agrobacterium T–DNA in *Arabidopsis thaliana* mediated by Cre recombinase." 1998, Nucleic Acids Research, vol. 26, pp. 2729–2734.*
Mariani, C. et al. "Induction of male sterility in plants by a chimaeric ribonuclease gene." 1990, Nature, vol. 347, pp. 737–741.*
Lloyd, A. M. and Davis, R. W. "Functional expression of the yeast FLP/FRT site–specific recombination system in *Nicotiana tabacum*." 1994, Mol Gen Genet, vol. 242, pp. 653–657.*

* cited by examiner

*Primary Examiner*—Anne Kubelik
(74) *Attorney, Agent, or Firm*—Winston & Strawn LLP

(57) ABSTRACT

The invention is drawn to a method of producing a male-sterile plant by using two different recombinases to generate different deletions in a transgenic construct in a plant, thereby resulting in a male-sterile plant with two different constructs in an allelic relationship to one another.

10 Claims, 2 Drawing Sheets

METHOD OF PRODUCING A MALE STERILE PLANT BY EXOGENIC ALLELISM

This is a continuation-in-part of U.S. Provisional Pat. Application No. 60/151,627, filed Aug. 31, 1999.

FIELD AND BACKGROUND OF THE INVENTION

The present invention relates to a novel concept in genetic engineering, according to which a eukaryotic organism is transformed and crossed so as to provide an offspring including a first exogene in a first chromosome of a chromosome pair and a second exogene in a second chromosome of the chromosome pair, the exogenes exhibiting allelic relationship, such that the exogenes obligatorily segregate to different gametes. The present invention further relates to expression cassettes for implementing the novel concept, to methods of implementing same for the obtainment of reversible male sterility in plants, and further to plants and plant products obtained thereby.

The gene is the basic functional unit of heredity. The gene concept was first set forth by Mendel in 1865 as a result of experiments conducted on pea plants. Mendel proposed that a genetic determinant of a specific character is passed on from one generation to the next as a unit without any blending of the units, a theory now known as the "one gene one trait" theory.

Two of mendel's proposed laws serve as the basis for modern genetics. Mendel's first law states that two members (alleles) of a gene pair obligatorily segregate to different gametes, such that one half of the gametes carry one member (allele) of the pair and the other half of the gametes carry the other member (allele) of the gene pair. Mendel's second law states that during gamete formation the segregation of alleles of a gene pair is independent of alleles other gene pairs.

Following Mendel's research, the discovery of chromosomes and the existence of linkage between genes closely positioned on a single chromosome have further contributed to our knowledge of inherited traits. Nowadays it is known that the second law of Mendel is valid for genes residing on different chromosomes and for genes residing on the same chromosome, provided that they are at least 50 centiMorgan apart, whereas for closer genes residing on the same chromosome, linkage dis-equilibrium is experienced.

Thus, in an individual, a genetic trait in it's simplest form is determined by a pair of closely related sequences known as alleles. Each allele, which is optionally an alternative form of a gene, resides on one of the chromosomes of a chromosome pair. The pair of alleles of a given individual can be identical in sequence or they can differ in sequence to various degree. In meiosis, which is the process of cell division which leads to the formation of sex cells (gametes), the chromosomes of any given chromosome pair segregate into different gametes. This chromosomal segregation is superseded by rearrangement of the DNA in chromosome pairs which takes place via inter chromosomal recombination events.

A specific trait of an individual is determined by a specific combination of two alleles carried by the individual. Thus, traits of an individual are determined by the genetic material inherited by that individual from both parents as determined by chromosomal segregation and recombination events in each of the individual's parents.

Alleles carried on a chromosome pair encode the same genetic trait. Allelic variance ensures a high degree of distinction between individuals.

Transformation of an exogene to a genome is typically random. Assuming one site of exogene integration, a resultant genome is said to be heterozygous of the type 1/0. By careful breeding and selection, a homozygous state for the exogene, i.e., 1/1 is obtainable. Although one can transform a genome with a second exogene (2), it is practically impossible, using conventional transformation techniques, to direct the second exogene to a given integration site, in a different genome. As such, using such conventional molecular biology and breeding techniques, it is practically impossible to achieve exogene allelism of the type 1/2.

Although it is theoretically possible to direct an exogene to a specific chromosomal site by gene knock-in techniques, which therefore could have been used to generate exogene allelism of the type 1/2, such techniques, are very poor in transformation yields. Indeed, no attempts of generating exogene allelism were made so far.

The production of hybrid plants has been practiced ever since the beginning of this century. Plant breeders discovered that crossing two distinct parental lines often resulted in a hybrid plant which displays what is termed as hybrid vigor or heterosis, which is characterized by an increased crop yield and/or adaptation to both biotic and abiotic stresses. Early on, hybrid plant production concentrated mainly on corn and sorghum which were found to benefit from crossing of well compatible parental lines. Later it was discovered that hybrid plant production is also applicable to other plant species.

Several explanations have been proposed for the existence of heterosis. It is clear that a wider allelic variety exist in hybrids plant lines as is compared to inbred plant lines, since the alleles present in a hybrid plant are inherited from two distinct parent plant lines. This allelic variety is favored as a likely explanation for hybrid vigor, however, at present no scientific evidence has been brought forth to support this explanation.

Since hybrid plants have been demonstrated to be superior to inbred lines with respect to yield and vigor, the development of hybrid seeds is one of the prime objectives of the seed industry. In addition, since hybrid plant varieties result from a unique combination, the possibility of duplicating or reusing the hybrid seeds is minimized, thus, providing breeders with an inherent commercial protection.

The production of hybrid seed on a large scale is challenging because many crops have both male and female reproductive organs (stamen and pistil) on the same plant, either within a single flower or in separate flowers. This arrangement results in a high level of self pollination and makes large scale directed crosses between parental lines to generate hybrid plants difficult to accomplish.

To guarantee that out-crossing will occur during the production of hybrid seed, breeders have either manually or mechanically removed stamens from one parental line. Although such manual emasculation is effective for some plants, such as wheat, it is labor intensive and impractical for plants with small bi-sexual flowers. To cross-pollinate such plants breeders have often resorted to using naturally occurring male sterile mutants in efforts to produce hybrid seeds. Although the use of naturally occurring male sterile mutants enables to cross pollinate plants with small bi-sexual flowers, the availability of such mutants and oftentimes the poor genetic makeup thereof severely limited wide spread use of this approach. In addition, using sterile mutants for out-crossing typically results in retention of sterility in a large fraction of the produced seeds. Such seeds when sown would then produce sterile plants which in the case of self pollinator crops such as wheat would lead to no crop yield for a fraction of the plants. To overcome the resultant low crop yield, a breeder is forced to select out the sterile seeds which can be a nearly impossible task.

Since important crops such as rice, wheat are self-pollinating plants with small bi-sexual flowers, there was a need and several attempts were made to develop systems for pollination control to assist in the production of F1 hybrids.

However, several conditions must exist in order to obtain economically feasible F1 hybrid plants. The male sterile line must be 100% sterile and yet female fertile, a natural pollen transfer from the male fertile line to the male sterile line must be facilitated, and in cases of grain or fruit crops, male fertility restoration (MFR) should be enabled in order to obtain crop yield in the F1 progeny.

There exist several mechanisms of male sterility in plants. One such mechanism is cytoplasmic male sterility (CMS). In general CMS has been used in corn, rice, sorghum and onion on a limited basis, see, for example, U.S. Pat. No. 3,861,079 to Patterson.

However, reliance on a single cytoplasmic-male-sterile system for the production of all hybrid plants is undesirable because it leaves the entire hybrid stock vulnerable to plant pathogens. For example, extensive use of one corn cytotype, cmsT lead to an eptiphytic outbreak of Southern Corn Leaf Blight in the early 1970's. Thus, it is important to develop alternative methods to produce male sterile lines in plant species where only a single male-sterility system is available.

An emerging alternative to cytoplasmic sterility is a nuclear sterility. Nuclear male-sterile-based pollination systems rely upon the introduction of a male sterility trait to one parental plant followed by the introduction of a fertility-restorer gene, as a result of cross-pollination, to produce fertile hybrid plants.

Typically, genetically engineered nuclear male sterility is effected by expressing, in a controlled and targeted manner, a protein toxin which destroys anther tissues of the plant in which it is expressed. The expression of this toxin can be either silenced or antagonized in the F1 progeny by the introduction of a fertility-restorer gene, as a result of cross-pollination.

Male reproductive processes in flowering plants occur in the anther. This organ is composed of several tissues and cell types, and is responsible for producing pollen grains that contain the sperm cells. A specialized anther tissue, the tapetum, plays an important role in pollen formation. The tapetum surrounds the pollen sac early in anther development, degenerates during the later stages of development and is not present as an organized tissue in the mature anther. The tapetum produces a number of proteins and other substances that either aid in pollen development or become components of the pollen outer wall. It is known that many male sterility mutations interfere with tapetum cell differentiation and/or function. Thus tapetal tissue is believed to be essential for the production of functional pollen grains.

As such, many nuclear male-sterile-based pollination systems known in the art utilize anther specific promoters to target the destruction of the tapetum or other anther specific tissues during maturation such that subsequent pollen development is arrested.

For example, U.S. Pat. Nos. 5,409,823, 5,659,124 and 5,824,542 to Crossland describe a dual method for producing male-sterile plants. Two genetically transformed plants, parents 1 and 2, are crossed to obtain male-sterile offspring. Parent 1 is transformed with an expression cassette comprising a nucleotide sequence encoding an anther-specific promoter which is operably linked to a nucleotide sequence encoding a trans-activator. Parent 2 is transformed with an expression cassette comprising a target nucleotide sequence, which is capable of being activated by the trans-activator, operably linked to a nucleotide sequence which encodes a toxin which can be an RNA or a polypeptide and which disrupts the formation of viable pollen. Therefore, crossing parent 1 with parent 2 results in male-sterile offspring. The male-sterile plants produced are useful for producing hybrid seed. Subsequent crossing of the male sterile plant with a plant which does not include the trans-activator restores fertility.

Although this system produces desirable male sterility in a portion of the produced offspring, restoration of fertility which relies upon the segregation of the trans-activator gene from the toxin gene cannot be efficiently effected using this system. In the male sterile plant the segregation of these two genes during meiosis relies a great deal on their physical chromosomal location, as such when a male sterile plant is crossed with a plant which does not express the trans-activator, the trans-activator and the toxin can be provided by the male sterile parent as a result of which a portion of the produced progeny will retain undesirable male sterility.

Thus the method by Crossland is not efficiently applicable for self pollinators such as, for example, wheat, cotton and rice.

U.S. Pat. No. 5,929,307 to Hodges describes a recombinant expression vector comprising a suicide gene flanked by site-specific recombination sequences, which vector, when introduced into a plant leads to male sterility. This invention further relates to a second expression vector including a recombinase gene which when introduced into the male sterile plant via a cross-pollinating restorer plant, leads to the deletion of the toxin gene and as a result to the restoration of fertility.

It will be appreciated in this case that since restoration of fertility is effected by a gene product which is introduced via a cross-pollinating restorer plant, a high copy number of the restorer gene must be maintained in the restorer plant such that highly efficient restoration of fertility in the resultant progeny is effected.

Thus, the presently available nuclear male-sterility pollination systems, although generally efficient in the production of male sterile plants, suffer from limitations when restoration of such male sterility via out-crossing is desirable, such as the case for grain or fruit producing hybrid plants. Since these systems cannot enable 100% restoration of fertility to the male sterile plants produced and since the resultant male sterile hybrid seeds are not typically selected out, a suboptimal crop yield from grain or fruit producing hybrid plants produced by these systems results.

There is thus a widely recognized need for, and it would be highly advantageous to have, a male sterile plant, which plant when out-crossed with a compatible male fertile plant generates male fertile offspring in substantially 100% of it's progeny. As further detailed hereinunder, such a plant can be generated by a transformation method which results in formation of allelism between two exogenes. There is thus a widely recognized need for, and it would be highly advantageous to have, a method and expression cassettes for the generation of exogene allelism.

SUMMARY OF THE INVENTION

It is one object of the present invention to provide a eukaryotic organism, such as an organism of the animalia or planta kingdom, or a commercially important product thereof, having a genome characterized by exogenic alletism, i.e., allelism of two distinct exogenes, which can be used to determine a phenotype of the organism.

It is another object of the present invention to provide expression cassettes which can be used by preplanned transformation and crossing regime to generate a eukaryotic organism having a genome characterized by exogenic allelism.

It is yet another object of the present invention to provide methods of generating exogenic allelism in a eukaryotic organism exploiting the expression cassettes of the former object of the invention.

It is still another object of the present invention to exploit the above methods and expression cassettes for the generation of substantially 100% reversible plant male sterility, exploitable, for example, in the hybrid seed industry of grain and fruit crops characterized by small, bi-sexual flowers.

Thus, according to one aspect of the present invention there is provided a non-human eukaryotic organism having a genome comprising a first exogene being in a first chromosome of a chromosome pair of the genome and a second exogene being in a second chromosome of the chromosome pair, the first and the second exogenes being in allelic relationship, such that the first and the second exogenes obligatorily segregate to different gametes.

According to further features in preferred embodiments of the invention described below, expression of the first and the second exogenes determines a phenotype of the organism.

According to still further features in the described preferred embodiments an expression product of the second exogene transactivates expression of the first exogene.

According to still further features in the described preembodiments the second exogene encodes an RNA polymerase.

According to still further features in the described preferred embodiments the second exogene encodes a transcription factor.

According to still further features in the described preferred embodiments the first exogene encodes a polypeptide selected from the group consisting of a cytotoxic polypeptide and a cytostatic polypeptide.

According to still further features in the described preferred embodiments the first exogene encodes an RNA molecule selected from the group consisting of an antisense RNA molecule and a ribozyme RNA molecule.

According to still further features in the described preferred embodiments expression products of the first and the second exogenes assemble into a hetero-oligomeric protein.

According to still further features in the described preferred embodiments the hetero-oligomeric protein has an activity selected from the group consisting of cytotoxic activity and cytostatic activity.

According to still further features in the described preferred embodiments the organism is a plant species.

According to still further features in the described preferred embodiments the second exogene encodes an RNA polymerase non-operable with eukaryotic promoters.

According to still further features in the described preferred embodiments the RNA polymerase is selected from the group consisting of bacterial RNA polymerase and bacteriophage RNA polymerase.

According to still further features in the described preferred embodiments the bacteriophage RNA polymerase is selected from the group consisting of T7 RNA polymerase, T3 RNA polymerase and SP6 RNA polymerase.

According to still further features in the described preferred embodiments the first exogene encodes a polypeptide selected from the group consisting of a cytotoxic polypeptide and a cytostatic polypeptide.

According to still further features in the described preferred embodiments the polypeptide is selected from the group consisting of pectate lyase, 1-3 β-glucanase, avidin, streptavidin, diphtheria Toxin A-chain (DTA), URF13, Indole acetic acid-lysine synthetase, CytA toxin and RNase-TI.

According to still further features in the described preferred embodiments the second exogene is under control of a eukaryotic tissue specific promoter, such that the first exogene is expressed in a specific tissue of the plant species.

According to still further features in the described preferred embodiments the specific tissue forms a part of an stamen tissue of the plant.

According to still further features in the described preferred embodiments expression of the first exogene and the second exogene results in male sterility of the plant.

According to another aspect of the present invention there is provided an expression cassette comprising (a) a first segment including a first transcribable polynucleotide sequence, the first transcribable polynucleotide sequence being operatively linked to a first promoter sequence, the first segment being flanked by a pair of first site-specific recombination sequences; and (b) a second segment, being linked to the first segment, the second segment including a second transcribable polynucleotide sequence, the second transcribable polynucleotide sequence being operatively linked to a second promoter sequence, the second segment being flanked by a pair of second site-specific recombination sequences.

According to yet another aspect of the present invention there is provided a method of generating exogenic allelism in a non-human eukaryotic organism, the method comprising the steps of (a) generating a first and second isogenic organisms homozygous for the expression cassette described hereinabove; (b) introducing a first recombinase into the first organism, so as to excise the first segment; (c) introducing a second recombinase into the second organism, so as to excise the second segment; and (d) crossing the organisms resultant from steps (b) and (c), so as to generate an offspring characterized by exogenic allelism.

According to further features in preferred embodiments of the invention described below, the first and the second pair of directly repeated site-specific recombination sequences are each independently selected from the group consisting of Lox recombination sequences, FRT recombination sequences, Gin recombinase sequences, Pin recombinase sequences and R/RS recombinase sequences.

According to still another aspect of the present invention there is provided an expression cassette comprising (a) a first segment including a first promoter sequence; (b) a second segment including a first transcribable polynucleotide sequence; and (c) a third segment including a second transcribable polynucleotide sequence, the second transcribable polynucleotide sequence being operatively linked to a second promoter sequence, the third segment being flanked by the first and second segments, wherein a pair of site-specific recombination sequences are disposed one between the first segment and the third segment and another between the second segment and the third segment, such that the first promoter sequence is operatively coupled with the first transcribable polynucleotide sequence only following excision of the third segment from the expression cassette by site specific recombination via the pair of site-specific recombination sequences.

According to an additional aspect of the present invention there is provided a method of generating exogenic allelism in a non-human eukaryotic organism, the method comprising the steps of (a) generating a first and a second isogenic organisms homozygous for the expression cassette described hereinabove; (b) introducing a recombinase into the first organism, so as to excise the third segment thereby operatively adjoining the first transcribable polynucleotide sequence to the first promoter sequence; and (c) crossing the organism resultant from step (b) and the second organism, so as to generate an offspring characterized by exogenic allelism.

According to further features in preferred embodiments of the invention described below, the first promoter sequence is a non-eukaryotic promoter sequence.

According to still further features in the described preferred embodiments the second promoter sequence is a tissue specific promoter sequence naturally operable in a first tissue.

According to still further features in the described preferred embodiments the first promoter sequence is a tissue specific promoter sequence naturally operable in a second tissue and further wherein the second transcribable polynucleotide sequence encodes a tissue specific transcription activator naturally expressed in the second tissue and naturally capable of activating the first promoter sequence.

According to still further features in the described preferred embodiments the second transcribable polynucleotide sequence encodes a transactivator.

According to still further features in the described preferred embodiments the transactivator is an RNA polymerase.

According to still further features in the described preferred embodiments the first transcribable polynucleotide sequence encodes an enzyme.

According to still further features in the described preferred embodiments the first transcribable polynucleotide sequence encodes an RNA molecule selected from the group consisting of an antisense RNA molecule and a ribozyme RNA molecule.

According to still further features in the described preferred embodiments the second transcribable polynucleotide sequence encodes a transactivator of the first promoter sequence.

According to yet an additional aspect of the present invention there is provided a plant homozygous for any of the expression cassettes herein described.

According to still an additional aspect of the present invention there is provided a plant comprising a genome, the genome including a pair of exogenes being in allelic relationship, wherein a first exogene of the pair of exogenes being located on a first chromosome of a chromosome pair of the genome of the plant, and further wherein a second exogene of the pair exogenes being located on a second chromosome of the chromosome pair of the genome of the plant.

According to further features in preferred embodiments of the invention described below, the first and second exogenes are selected such that expression thereof generates male sterile plant.

According to still further features in the described preferred embodiments by crossing the male sterile plant with a male fertile plant results in offsprings characterized by male fertility.

According to a further aspect of the present invention there are provided plant seeds each of which comprising a genome, the genome including a pair of exogenes being in allelic relationship, wherein a first exogene of the pair of exogenes being located on a first chromosome of a chromosome pair of the genome of the plant seeds, and further wherein a second exogene of the pair of exogenes being located on a second chromosome of the chromosome pair of the genome of the plant seeds.

The present invention successfully addresses the shortcomings of the presently known configurations by providing a eukaryotic organism having a genome characterized by exogenic allelism, i.e., allelism of two distinct exogenes, which can be used to determine a phenotype of the organism, expression cassettes and methods useful in the generation of such an organism.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention. In this regard, no attempt is made to show structural details of the invention in more detail than is necessary for a fundamental understanding of the invention, the description taken with the drawings making apparent to those skilled in the art how, the several forms of the invention may be embodied in practice.

In the drawings.

DESCRIPTION OF THE PREFERRED EMBODIMENTS

Figure 1:
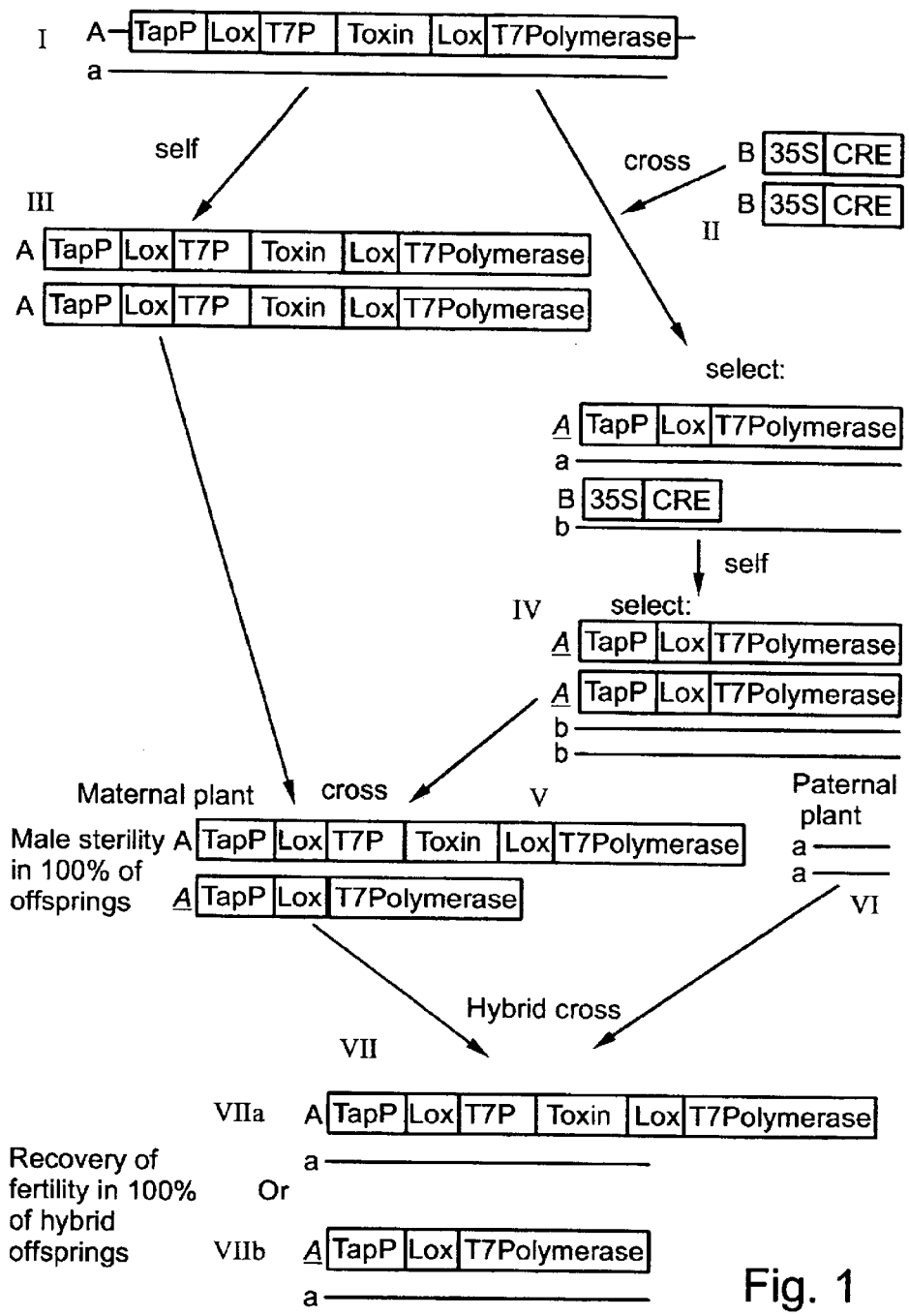
FIG. 1 is a flow diagram outlining one method for generating plants according to the teachings of the present invention. TapP—tapetum promoter; Lox—Cre recombinase recognition site; T7P—bacteriophage T7 promoter; T7 polymerase—the bacteriophage RNA polymerase recognizes the T7 promoter site; 35S—the CaMV promoter; CRE—the CRE recombinase.

The present invention reduces to practice a novel concept in genetic engineering, according to which a eukaryotic organism is transformed and crossed so as to provide an offspring including a first exogene in a first chromosome of a chromosome pair and a second exogene in a second chromosome of said chromosome pair, the exogenes exhibiting allelic relationship, such that the exogenes obligatorily segregate to different gametes. The present invention is further of expression cassettes for implementing the novel concept, methods of implementing same for the obtainment of reversible male sterility in plants, and plants and plant products obtained thereby.

The principles and operation of a methods and cassettes for generating exogenic allelism in a non-human eukaryotic organism according to the present invention may be better understood with reference to the drawings and accompanying descriptions.

Before explaining at least one embodiment of the invention in detail, it is to be understood that the invention is not limited in its application to the details of construction and the arrangement of the components set forth in the following description or illustrated in the drawings. The invention is capable of other embodiments or of being practiced or carried out in various ways. Also, it is to be understood that the phraseology and terminology employed herein is for the purpose of description and should not be regarded as limiting.

According to one aspect of the present invention there is provided a non-human eukaryotic organism having a genome comprising a first exogene in a first chromosome of a chromosome pair of the genome and a second exogene in a second chromosome of the chromosome pair. The first and second exogenes exhibiting allelic relationship, such that they obligatorily segregate to different gametes when such gametes form in the organism.

It will be appreciated that since non-human eukaryotic organisms contain a plurality of chromosome pairs, an allelic relationship of two exogenes can be established on more than one chromosome pair and in more than one location on a given chromosome pair.

As used herein the phrase "allelic relationship" and the term "allelism" refer to the positional relationship between two genes on two chromosomes of a chromosome pair. As such "exogenic allelism" is the allelic positioning of two functionally distinct exogenes on the chromosomes of a chromosome pair such that substantially 100% segregation of the two exogenes is observed upon gamete formation.

As used herein the term "exogenes" refers to polynucleotide sequences which are trans-introduced into and integrated in a genome of a species. Such exogenes may be of a different or the same species. Exogenes according to the present invention include transcribable sequences, e.g., mRNA and protein coding sequences, both cDNA and genomic sequences, and antisense RNA coding sequences, and/or cis acting sequences which cis-control gene expression, such as promoters and enhancers. Such exogenes, assembled in an expression cassette, are used to transform cells and/or organisms to thereby obtain transformed, genetically modified or transgenic cells and/or organisms harboring the exogene(s) in their genome. A transgenic organism is a stably transformed organism having one or more cells that contain an exogene. The term stably transformed refers to a transformed cell or organism (host) that is capable of transmitting an exogene to its progeny. According to the present invention a stably transformed host has an exogene integrated into its genome. Exogenes according to the present invention may represent sequences which naturally occur in the organism, or mutants, portions and chimeras thereof or sequences which do not naturally occur in the organism, for example sequences from a different sub species, species or genus.

According to a preferred embodiment of the present invention the expression of the first and the second exogenes determines a phenotype of the organism. As used herein the term "phenotype" refers to characteristic gene and/or exogene expression which results in the presence of distinct molecular product(s) in an organism. The presence of such molecular product(s) such as for example a protein or an RNA molecule (e.g. mRNA or antisense RNA) may lead to morphological changes, differential resistivity to pathogens and chemicals, differentiated development and the like.

Thus, the expressed exogenes co-affect the phenotype of an organism, that is to say that the presence of expression products from both exogenes is required in order to achieve a certain phenotype.

The term "expression" refers to the biosynthesis of a gene product. For example, in the case of a structural gene, expression involves the transcription of the structural gene into messenger RNA (mRNA) and the translation of the mRNA into one or more polypeptides. In the case of antisense RNA or ribozymes the expression product is an RNA molecule.

A trait determined by two allelic exogenes is particularly advantageous and is the gist of the present invention since crossing a transgenic organism characterized by exogenic allelism with a second organism leads to the complete segregation of the two exogenes and as such to loss of the phenotype in the offsprings. This cannot be achieved for traits determined by a single gene or even a multiplicity of genes arranged in a non-allelic fashion, since complete segregation of these genes and as such loss of the trait cannot be ensured. The advantages of exogenic allelism are further exemplified hereinbelow with respect to plants characterized by exogenic allelism.

According to one preferred embodiment of the present invention an expression product of the second exogene transactivates expression of the first exogene.

The transactivators of the present invention include, but are not limited to, polymerases, DNA binding proteins, naturally occurring and synthetic transcriptional activators, translational activators, post-transcriptional activators, and the like. It will be appreciated that only transactivators which do not naturally occur in the cells or tissue in which they are to be expressed are selected. Preferably, transactivators from unrelated organisms are selected.

According to one preferred embodiment of the present invention the transactivator is a bacteriophage RNA polymerase. The use of such transactivator polypeptides in directing expression of another nucleotide sequence is exemplified by the T7 RNA polymerase. See, U.S. Pat. Nos. 5,122,457; 5,126,251; and 5,135,855; Lassner et al. (1991) Plant Molecular Biology 17:229–2; Rodriguez et al. (1990) Journal of Virology 64:4851–4857; Vennema et al. (1991) Gene 108:201–210; Benton et al., Molecular and Cellular Biology (1990) Molecular and Cellular Biology 10:353–360; Elroy-Stein and Moss (1990) Proceedings, Proc. Natl. Acad. Sci.:USA 87:6743–6747; Moss et al. (1990) Nature 348:91–92; Elroy-Stein et al. (1989) Proceedings, Proc. Natl. Acad. Sci.:USA 86:6126–6130; and Rosenberg et al. (1987) Gene 56:125–135, herein incorporated by reference. It will be appreciated that other polymerases which do not normally exist in the organism such as, for example, polymerases from species different than that of the organism but yet of the same genus, can also be utilized by the present invention.

Transactivators also include transcriptional activators which are necessary for transcription activation of specific promoters. Binding domains of one protein may be fused to activity domains of another protein to form chimeras of such DNA binding proteins, such as GAL4/VP16 (Carey et al. (1989), J. Mol. Biol., 209:423–432; Cress et al. (1991) Science, 251:87–90; and Sadowski et al. (1988), Nature, 335:563–564). Likewise, the binding domain of other proteins, i.e., Lex A (Brent and Ptashne, (1985), Cell, 43:729–736, which describes a Lex A/GAL4 transcriptional activator) can be utilized.

Transactivators can also be translational activators. Translational activators are exemplified by the cauliflower mosaic virus translational activator (TAV). See, for example Futterer and Hohn (1991) EMBO J. 10:3887–3896. In this system a dicistronic mRNA is produced. That is, two coding regions are transcribed in the same mRNA from the same promoter. In the absence of TAV, only the first cistron is translated by the ribosomes. However, in cells expressing TAV, both cistrons are translated.

Thus, when expressed, the transactivator transactivates the expression of the first exogene. Thus, it is the expression of the first exogene which determines the phenotype of the organism, but since the expression of the first exogene is dependent on the presence of the second exogene product, both must be expressed in order to establish and maintain a phenotype.

According to preferred embodiments of the present invention the first exogene encodes a molecule which can either arrest cell proliferation and/or cause cell degeneration.

Thus, according to one preferred embodiment of the present invention the first exogene encodes a cytotoxic polypeptide or a cytostatic polypeptide. The expression of the first exogene either prevents the cell in which it is expressed from proliferating or alternatively it causes cell degeneration and ultimately cell death. Specific examples of cytostatic and cytotoxic polypeptides are further described hereinbelow.

In an alternative embodiment, the first exogene encodes an antisense RNA or a ribozyme which when transcribed target specific mRNA sequences expressed within the cell and as such can be used, for example, to disrupt biological processes and bring about cell death.

According to another preferred embodiment of the present invention the expression products of the first and the second exogenes assemble into a hetero-oligomeric protein. In this case both exogenes are preferably concomitantly expressed such that accumulation of the two non-functional expression products leads to assembly of a functional hetero-oligomer.

The first and second exogenes are also referred to hereinbelow as the first and second transcribable polynucleotide sequences.

According to another aspect of the present invention there is provided an expression cassette useful in generating exogenic allelism in a non-human eukaryotic organism. The expression cassette according to this aspect of the present invention includes a first segment including a first promoter sequence. The expression cassette further includes a second segment including a first transcribable polynucleotide sequence and a third segment flanked by the first and second segments and including a second transcribable polynucleotide sequence operatively linked to a second promoter sequence. A pair of site-specific recombination sequences are disposed one between the first segment and the third segment and another between the second segment and the third segment. Thus, the first promoter sequence can be operatively coupled with the first transcribable polynucleotide sequence following excision of the third segment from the expression cassette by site specific recombination via the pair of site-specific recombination sequences.

As used herein an expression cassette is a polynucleotide molecule comprising at least one polynucleotide sequence that is expressed in a host cell or organism. Typically such expression is under the control of certain cis acting regulatory elements including constitutive, inducible or tissue-specific promoters, and enhancer elements. Common to the art, such polynucleotide sequence(s) are said to be "operably linked to" the regulatory elements. Expression cassettes typically also include eukaryotic or bacterial derived selectable markers that allow for selection of eukaryotic cells containing the expression cassette. These can include, but are not limited to, various genes which confer antibiotic resistance and which are well known in the art and therefore will not be further described herein.

For many applications it is required that the expression cassette described herein will be integrated in a nucleic acid construct, such as an expression construct or an antisense construct. Such constructs are well known in the art, are commercially available and may include additional sequences, such as, for example, a cloning site, one or more prokaryote or eukaryote marker genes with their associated promoters for selection of prokaryotic cells containing the expression cassette, one or more prokaryotic origins of replication, one or more translation start site, one or more polyadenylation signal, and the like.

A construct according to the present invention preferably further includes an appropriate selectable marker. In a more preferred embodiment according to the present invention the construct further includes an origin of replication. In another most preferred embodiment according to the present invention the construct is a shuttle vector, which can propagate both in E. coli (wherein the construct comprises an appropriate selectable marker and origin of replication) and be compatible for propagation in cells, or integration in the genome, of an organism of choice. The construct according to this aspect of the present invention can be, example, a plasmid, a bacmid, a phagemid, a cosmid, a phage, a virus or an artificial chromosome.

To be expressed, polynucleotide sequences included in an expression cassettes must be driven by a promoter. Several types of promoters are now well known in the art of transformation, as are other regulatory elements that can be used alone or in combination with such promoters.

As used herein the term "promoter" includes reference to a region of DNA upstream from the start of transcription and involved in recognition and binding of RNA polymerase and other proteins which are required to initiate transcription. Promoters which initiate transcription only in certain tissues are referred to as "tissue-specific". A "cell type" specific promoter primarily drives expression in certain cell types in one or more organs.

According to a preferred embodiment of the present invention the second promoter of the expression cassettes described hereinabove, and which drives the expression of the transactivator is a tissue specific promoter. It will be appreciated, however, that other types of promoters such as inducible promoters, constitutive promoters and developmentally regulated promoters can also be used by the present invention depending on the desired spatial and temporal expression of the phenotype determined by the exogenic allelism.

Specific examples to polynucleotide sequences and promoters are detailed hereinbelow with respect to the plant embodiments of the present invention which are further exemplified in Examples 1 and 2 of the Examples section.

A number of different site-specific recombinase systems can be utilized in accordance with the present invention, including, but not limited to, the Cre/lox system of bacteriophage P1, the FLP/FRT system of yeast, the Gin recombinase of phage Mu, the Pin recombinase of E. coli, and the R/RS system of the pSR1 plasmid. The presently two preferred site-specific recombinase systems are the bacteriophage P1 Cre/lox and the yeast FLP/FRT systems, for these systems have shown to have high recombination yields by others. The site specific recombination sequence for each of these two systems is relatively short (34 bp for lox and 34–47 bp for FRT). In these systems a recombinase (Cre or FLP) interacts specifically with its respective site-specific recombination sequence (lox or FRT, respectively) to invert or excise the intervening sequences depending on the orientation of the site-specific recombination sequences. The site specific recombination sequences utilized by the expression cassettes of the present invention are oriented as direct repeats, so as to affect excision of the sequence flanked thereby. Site-specific recombination systems are further described in U.S. Pat. No. 5,527,695, which is incorporated herein by reference.

As mentioned hereinabove, to effect excision a suitable recombinase is introduced into the target organism by any suitable method which leads to the expression of the recombinase within the organism. For example, the recombinase gene may be stably integrated into the genome of the organism or alternatively transiently expressed therein. As further detailed hereinbelow with respect to plants, a recombinase can also be introduced into a plant via sexual crossing with a transgenic plant carrying the recombinase gene. Similar crossings can be made between, for example, inbred organisms of the animalia kingdom.

To generate exogenic allelism in the organism, the above described expression cassette is introduced into the genome of the organism by transformation methods known in the art, some of which are described in detail below.

Following establishment of a stably transformed organism, a first and a second isogenic organisms homozygous for the expression cassette are propagated therefrom. A recombinase gene specific for the site specific recombinase sequences is introduced into the first organism, so as to excise the third segment thereby operatively adjoining the first transcribable polynucleotide sequence to the first promoter sequence. As already mentioned, the recombinase gene is either introduced via transformation techniques or preferably via out-crossing with a recombinase expressing organism which does not contain the expression cassette, but which is preferably isogenic to the first organism.

Finally the resultant first and second organisms are crossed so as to generate an offspring characterized by exogenic allelism. Since each organism contributes a single chromosome of a chromosome pair to it's offspring, such an offspring will contain as a part of it's genome a first expressible polynucleotide on a first chromosome of a chromosome pair and a second expressible polynucleotide on a second chromosome of the chromosome pair, wherein the first and second expressible polynucleotides exhibit allelism, i.e., such polynucleotides obligatorily segregate to different gametes.

It will be appreciated that when a single pair of site specific sequences is used, the expression cassette positioning of the first polynucleotide coding sequence and the second polynucleotide coding sequence can be switched around.

As is further exemplified hereinabove the first transcribable polynucleotide sequence encodes a cytotoxic or cytostatic molecule and the second polynucleotide encodes a transactivator. In this case the expression of the transactivator will be dependent on the type of the second promoter used and will most typically be, in cases wherein a constitutive or tissue specific promoter is used, initiated following transformation of the expression cassette into the organism. On the other hand, in an alternative polynucleotide sequences arrangement of this expression cassette, the transactivator can be encoded by the first transcribable polynucleotide sequence, while the cytotoxic or cytostatic molecule can be encoded by the second transcribable polynucleotide sequence. Thus, in this case the transactivator will be expressed only following recombination. As such, in the latter configuration, which is described in more detail hereinbelow in Example 1 of the examples section, expression from any exogenic sequences will initiate only following recombination. This is particularly advantageous in situations wherein the transactivator is toxic to the cell in which it is expressed. In such cases premature expression of the transactivator must be avoided.

As is further detailed hereinunder, exogenic allelism can also be generated using an expression cassette which utilizes two pairs of site specific recombination sequences.

Thus, according to another aspect of the present invention there is provided an expression cassette useful in generating exogenic allelism in a non-human eukaryotic organism. The expression cassette according to this aspect of the present invention includes a first segment flanked by a pair of first site-specific recombination sequences and including a first transcribable polynucleotide sequence, wherein the first transcribable polynucleotide sequence is operatively linked to a first promoter sequence.

The expression cassette according to this aspect of the present invention further includes a second segment, linked to the first segment, the second segment including a second transcribable polynucleotide sequence operatively linked to a second promoter sequence, wherein the second segment is flanked by a pair of second site-specific recombination sequences.

Following establishment of a stably transformed organism using the above cassette via transformation as is further detailed hereinbelow, a first and a second isogenic organisms, homozygous for the expression cassette, are propagated therefrom. A first recombinase gene is introduced, as described above, into the first organism, so as to excise the first segment. A second recombinase gene is introduced, as described above, into the second organism, so as to excise the second segment.

Finally the resultant first and second organisms are crossed so as to generate an offspring characterized by exogenic allelism.

As before, since each organism contributes a single chromosome of a chromosome pair to it's offspring, such an offspring will contain as a part of it's genome a first expressible polynucleotide on a first chromosome of a chromosome pair and a second expressible polynucleotide on a second chromosome of the chromosome pair. Further related description of the expression cassette according to this aspect of the present invention is given hereinbelow in Example 2.

According to yet another aspect of the present invention and as demonstrated in Examples 1 and 2 of the examples section exogenic allelism is used to generate reversible nuclear male sterility in plants.

Male sterility is the failure or inability to produce functional or viable pollen. Male sterility may result from defects leading to the non-formation of pollen or to the lack of functional ability in the pollen when it is formed. Therefore, either pollen is not formed or, if formed, it is either nonviable or incapable of effective fertilization under normal conditions.

The male-sterile plants of the present invention, are female fertile. That is, the plants do not produce fertile pollen, yet are capable of accepting pollen from the desired paternal parent resulting in fertilization and hybrid seed production.

To effect male sterility in a plant, the two transcribable polynucleotide sequences must be expressed such that when expressed cytostatic or cytotoxic activity only occurs in the stamen tissue or tissues (e.g., anther, pollen or tapetum).

Thus, according to a preferred embodiment of this aspect of the present invention, the second promoter is an stamen tissue-specific promoter. As used herein the term "stamen" refers to the male fertilizing organ of a flowering plant, including anther tissues. As used herein the phrase "anther tissues" or the term "anther" is meant to include the pollen and tapetum tissues as well.

In the case of promoter DNA sequences, stamen specific promoters are typically specific to the anther tissues and include regulatory sequences which direct the transcription of associated transcribable sequences so that the corresponding RNA is present in anther tissues in concentrations at least 100-fold that observed in other tissues.

Anther-specific promoters are well known in the art, examples of which include, but are not limited to, a tapetum-specific promoter such as the tobacco anther promoter, ant32, an anther-specific promoter such as that from LAT52 (Twell et al., Mol. Gen. Genet. 217: 240–245 (1989)); a pollen-specific promoter such as that from Zm13 (Guerrero et al., Mol. Gen. Genet. 224: 161–168 (1993)) or a microspore-preferred promoter such as that from apg (Twell et al., Sex. Plant Reprod. 6: 217–224 (1993). Additional examples are provided in, for example, U.S. Pat. No. 5,477,002, which discloses promoter sequences from anther-specific genomic clones which are operatively linked to a DNA sequence coding for a desired polypeptide to enable anther specific expression.

By utilizing stamen-specific promoters, the resulting transgenic plants will express the transactivator only in the stamen tissues of the plant.

As already mentioned hereinabove, a transactivator expressed from the second transcribable polynucleotide sequence of an expression cassette can be an RNA polymerase, a transcriptional activator or a translational activator.

In a preferred embodiment of this aspect of the present invention the transactivator is a bacteriophage RNA polymerase such as, but not io limited to, a T7 RNA polymerase, a T3 RNA polymerase or an SP6 RNA polymerase.

As such the first promoter which drives the expression of the first transcribable polynucleotide sequence includes a sequence recognizable by bacteriophage RNA polymerase such that in the presence of the bacteriophage RNA polymerase and providing operational linkage between the first transcribable polynucleotide sequence and the first promoter, transcription of the first polynucleotide sequence is effected.

According to a preferred embodiment of this aspect of the invention the expression product of the first transcribable polynucleotide sequence is utilized to disrupt formation of viable pollen when expressed.

As mentioned hereinabove the resultant expression product of the first transcribable polynucleotide sequence can be either a polypeptide or an RNA molecule such as for example an anti-sense RNA molecule or a ribozyme RNA molecule.

Examples of polypeptides suitable for use in this aspect of the present invention include, but are not limited to, proteins capable of inhibiting the synthesis of macromolecules that are essential for cellular function, enzymes that degrade macromolecules that are essential for cellular function, proteins that alter the biosynthesis or metabolic metabolism of plant hormones and proteins that inhibit a specific function or development of anther/tapetum cells.

For example, Mariani et al., Nature, 347:737, (1990), have shown that expression of either Aspergillus oryzae RNase-T1 or an RNase of Bacillus amyloliquefaciens, designated "BARNASE", in the tapetal cells of a plant induced destruction of the tapetal cells, resulting in male sterility. Other genes can be used as alternatives to BARNASE for the development of male sterile plants, such as an anther-specific β-1,3-glucanase (Hird et al. The Plant Journal 4:1023–1033, 1993), or the male sterility gene described by Aarts et al. Nature 363: 715–717, 1993.

Additional polypeptides include diphtheria Toxin A-chain (DTA), which inhibits protein synthesis, Greenfield et al. (1983), Proc. Natl. Acad., Sci.:USA, 80:6853; Palmiter et al. (1987), Cell, 50:435; Pectate lyase pelE from Erwinia chrysanthemi EC16, which degrades pectin, causing cell lysis. Keen et al. (1986), J. Bacteriology, 168:595; T-urf13 (TURF-13) from cms-T maize mitochondrial genomes; this gene encodes a polypeptide designated URF13 which disrupts mitochondrial or plasma membranes. Braun et al. (1990), Plant Cell, 2:153; Dewey et al. (1987), Proc. Natl. Acad. Sci.:USA, 84:5374; Dewey et al. (1986), Cell, 44:439; Gin recombinase from phage Mu a gene, which encodes a site-specific DNA recombinase which will cause genome rearrangements and loss of cell viability when expressed in cells of plants. Maeser et al. (1991), Mol. Gen. Genet., 230:170–176; Indole acetic acid-lysine synthetase (iaaL) from Pseudomonas syringae, which encodes an enzyme that conjugates lysine to indole acetic acid (IAA). When expressed in the cells of plants, it causes altered developments due to the removal of IAA from the cell via conjugation. Romano et al. (1991), Genes and Development, 5:438–446; Spena et al., Mol. Gen. Genet., (1991), 227:205–212; Roberto et al. (1992 XXX) Proc. Natl. Acad. Sci.:USA, 87:5795–5801; CytA toxin gene from Bacillus thuringiensis Israeliensis which encodes a protein that is mosquitocidal and hemolytic. When expressed in plant cells, it causes death of the cell due to disruption of the cell membrane. McLean et al. (1987), J. Bacteriology, 169:1017–1023; Ellar et al. (1990), U.S. Pat. No. 4,918,006; and, biotin binding proteins such as Streptavidin and avidin as further detailed in WO 96/40949 and 99/04023 which describe the use of a biotin binding protein for the induction of male sterility.

In addition, the first polypeptide sequence can also encode DNAse, RNAse; protease; salicylate hydroxylase and the like.

In cases where it may be beneficial to target the polypeptide product expressed from the first transcribable polynucleotide sequence to a subcellular compartment such as the chloroplast, vacuole, peroxisome, glyoxysome, cell wall or mitochondrion, or for secretion into the apoplast, the first transcribable polynucleotide sequence includes a signal sequence, 5' and/or 3' to the region of the polypeptide encoding sequence. Targeting sequences at the 5' and/or 3' end of the structural gene may determine, during protein synthesis and processing, where the encoded protein is ultimately compartmentalized. The presence of a signal sequence directs a polypeptide to either an intracellular organelle or subcellular compartment or for secretion to the apoplast. Many sigsequences are known in the art. To this end, see, for example, Becker et al., Plant Mol. Biol. 20: 49 (1992), Close, P. S., Master's Thesis, Iowa State University (1993), Knox, C., et al., "Structure and Organization of Two Divergent Alpha-Amylase Genes From Barley", Plant Mol.

Biol. 9: 3–17 (1987), Lerner et al., Plant Physiol. 91: 124–129 (1989), Fontes et al., Plant Cell 3: 483–496 (1991), Matsuoka et al., Proc. Natl. Acad. Sci. 88: 834 (1991), Gould et al., J. Cell Biol 108: 1657 (1989), Creissen et al., Plant J. 2: 129 (1991), Kalderon, D., Robers, B., Richardson, W., and Smith A., "A short amino acid sequence able to specify nuclear location", Cell 39: 499–509 (1984), Stiefel, V., Ruiz-Avila, L., Raz R., Valles M., Gomez J., Pages M., Martinez-Izquierdo J., Ludevid M., Landale J., Nelson T., and Puigdomenech P., "Expression of a maize cell wall hydroxyproline-rich glycoprotein gene in early leaf and root vascular differentiation", Plant Cell 2: 785–793 (1990).

Alternatively male sterility can be induced by the expression of an antisense RNA. The binding of an antisense messenger RNA molecule to target messenger RNA (mRNA) molecules results in RNaseH associated degradation of the mRNA and/or arrest of translation. Thus, a suitable antisense molecule would have a sequence that is complementary to that of a messenger RNA species encoding a protein that is essential for tapetal cell function or pollen synthesis.

For example, an antisense RNA that interferes with the expression of the RTS2 gene product can be utilized by the present invention. Alternatively, the antisense of PRK1 (pollen-expressed receptor-like kinase) from *Petunia inflata* (Mu et al. The Plant Cell 6:709–721, 1994), or the antisense directed against the Bcp1 male fertility gene of Arabidopsis (Xu et al. Proc. Natl. Acad. Sci. 92: 2106–2110, 1995) can also be utilized as an antisense RNA according to the present invention. In addition an antisense RNA molecule can be directed to a nuclear localization signal sequence and as such bring about degradation and/or arrest of translation of mRNA species which contain NLS signal sequences.

The first polynucleotide can also encode a ribozyme. Ribozymes can be designed to express endonuclease activity that is directed to a certain target sequence in a messenger RNA molecule. For example, Steinecke et al., EMBO J., 11:1525, (1992), achieved up to 100% inhibition of neomycin phosphotransferase gene expression by ribozymes in tobacco protoplasts. Alternatively, an RNA molecule capable of promoting RNaseP-mediated cleavage of target messenger RNA molecules can also be used. According to this approach, an external guide sequence can be constructed for directing the endogenous RNaseP to a particular species of intracellular messenger RNA which is subsequently cleaved thereby. See Altman et al., U.S. Pat. No. 5,168,053 and Yuan et al., Science, 263:1269, (1994).

According to another preferred embodiment of the present invention the expression products of the first and second polynucleotides form a hetero-oligomer, e.g., a heterodimer. Such a hetero-oligomer can be, for example, an enzyme which displays cytotoxic activity. Thus, according this aspect of the present invention the first and second promoters are both stamen-specific promoters, as a result of which both polynucleotides are expressed and their polypeptide products assembled in staminal tissue, such as for example anther tissue, so as to cause degeneration of anther tissue which ultimately leads to male sterility.

To generate exogenic allelism in plants any one of the expression cassettes described hereinabove must first be used to transform plant tissue from which transgenic plants can be reconstituted.

As is further detailed above the term "transformation" describes a process by which an exogene such as an expression cassette enters and changes a recipient cell into a transformed, genetically modified or transgenic cell. Transformation may rely on any known method for the insertion of foreign nucleic acid sequences into a eukaryotic host cell. The principle methods of effecting stable integration of exogenous DNA into plant genomic DNA include, Agrobacterium-mediated gene transfer, direct DNA uptake, including methods for direct uptake of DNA into protoplasts, electroporation of DNA, injection of DNA into plant cells or tissues, biolistic bombardment of DNA coated particles, direct incubation of DNA with germinating pollen and the use of plant viruses as gene vectors. These methods are well described in the art an as such no further description is provided herein.

By applying any one of the methods for generating exogenic allelism described hereinabove, resultant male sterile, female fertile plants can be obtained. Such male sterile plants, when out-crossed with a male fertile plant yield male fertile hybrid seeds in 100% of the progeny obtained.

Thus, two exogenous and distinct polynucleotide sequences which exhibit allelic relationship, can be co-expressed within the same transgenic plant and as a result of which induce male sterility. Subsequent segregation of these sequences leads to recovery of fertility in 100% of the cases. Such segregation will be observed in 100% of the offsprings when such a plant is crossed with a compatible non-transgenic plant. As such, exogenic allelism can be used to generate male sterility in plants, which male sterility is 100% reversible in subsequent generations. This is of particular advantage since recovery of fertility is of particular importance in hybrid crop production in which seeds or fruits are collected. Such complete recovery of fertility can only be achieved by complete segregation of the two polynucleotide sequences and as such it can only be achieved for sequences which are disposed within the genome of the plant in allelic relationship. As such, complete segregation and as a result complete recovery of fertility are ensured by the methods and expression cassettes of the present invention.

It will be appreciated that the methods and constructs of the present invention can be used to generate reversible male sterility in both fruit and non-fruit producing plants. Example of fruit producing plants include but are not limited to, wheat, barley and rice, while examples to non-fruit producing plants include, but are not limited to, lettuce, cauliflower and cabbage. Of particular importance are plants from which fruits are harvested such as grains, since the resultant hybrid seeds must be male fertile such that plants grown from such seeds bear fruit which can be harvested. In this case 100% recovery of fertility is of economic importance since all of the resultant progeny from the hybrid cross will produce fruit. It will be appreciated by one of skill in the art that the expression cassettes and methods described herein can also be applied to animalia.

For example, exogenic allelism can be used to express equal-molar amounts of two distinct exogenes which may otherwise be subjected to differential positional effects. For example a cell culture derived from cell of an animal characterized by exogenic allelism can be used to express two distinct exogenes in substantially equal-molar amounts since both exogenes are positioned in an identical position on two chromosomes of a chromosome pair. As a result these exogenes will be subjected to the same positional effect if any and as such will be expressed in substantially equal-molar amounts. It will be appreciated in this case that identical promoter sequences are employed upstream to the two exogenic sequences.

It will be appreciated that methods of animal cell transformation and generation of transgenic animals are well known in the art. Such methods are further described in the manual and text books listed in the preamble of the Examples section below.

Thus, the present invention provides methods and expression cassettes with which exogenous allelism can be generated in a non-human eukaryotic organism. Such allelism can be of great utility in cases where complete segregation of the allelic exogenes is desirable in subgenerations, such as the case of male sterile plants and their resultant male fertile hybrid progeny.

Additional objects, advantages, and novel features of the present invention will become apparent to one ordinarily skilled in the art upon examination of the following examples, which are not intended to be limiting. Additionally, each of the various embodiments and aspects of the present invention as delineated hereinabove and as claimed in the claims section below finds experimental support in the following examples.

EXAMPLES

Reference is now made to the following examples, which together with the above descriptions, illustrate the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I–III Ausubel, R. M., ed. (1994); Cell Biology: A Laboratory Handbook" Volumes I–III Cellis, J. E., ed. (1994); "Current Protocols in Immunology" Volumes I–III Coligan J. E., ed. (1994); "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods and Enzymology" Vol. 1–317 Academic Press; all of which are incorporated by reference as if fully set forth herein. Other general references are provided throughout this document. The procedures therein are believed to be well known in the art and are provided for the convenience of the reader. All the information contained therein is incorporated herein by reference.

Example 1

Example 1 describes an expression cassette suitable for the generation of allelism in a plant, which allelism is used to generate 100% reversible male sterility. Since hybrid seed production is of commercial importance and since complete recovery of male fertility is crucial for high grain crop yields a system was developed which allows for the generation of male sterility but at the same time allows complete recovery of male fertility in progeny resultant from an outcross such as, for example, a hybrid outcross. As such this system can be used with high efficiency in hybrid seed production.

It will be appreciated that methods pertaining to plant self crossing and outcrossing utilized herein for the propagation of transformed plants and for subsequent hybrid seed production are commonly practiced in the art and as such no further description is necessary.

FIG. 1 outlines one method for generating reversible male sterile plants according to the teachings of the present invention.

Plant tissue is transformed with cassette I by, for example, an agrobacterium mediated gene transfer method and transgenic issue is regenerated into identical transgenic plants which harbor a single copy of cassette I. Cassette I includes a Tapetum specific promoter (TapP) such as ant32 or any other suitable stamen tissue specific promoter, followed by a LOX direct repeat. Following the LOX sequence is a T7 promoter region (T7P) which is recognized by the bacteriophage T7 polymerase which is not normally produced in plants. As such expression from the T7 promoter requires the presence of exogenous T7 polymerase gene or gene product. The T7 promoter is operatively linked to a cell cytotoxic molecule coding sequence designated as the toxin. In the presence of a T7 polymerase the toxin is expressed from the T7 promoter. A toxin which can be used in accordance with the present invention encodes a protein or an RNA molecule capable of disrupting the production of functional pollen cells or the formation of pollen as further detailed hereinabove. The toxin gene is followed by a second Lox site (direct repeat) which is followed by a T7 polymerase gene which is not linked to an operable promoter.

The transgenic plant including this cassette is crossed with an isogenic plant which is homozygous for a recombinase gene (CRE) expressible under a strong constitutive promoter such as the 35 S promoter but which does not contain cassette I. The transgenic plant including cassette I is also selfed to obtain a homozygote (III).

The plant resultant from cross II is selfed to obtain a plant containing cassette IV. Cassette IV results from the excision of the toxin and the T7 promoter regions. This excision brings the T7 polymerase region in close proximity to the TapP promoter region (separated by the Lox site which is 34 bp in length) such that the T7 polymerase gene is now under the transcriptional control of the TapP promoter. The plants harboring cassette IV will express the T7 polymerase in tapetal cells which should have no deleterious effects on pollen production. It will be appreciated in this case that since the direct repeat (Lox) site is immediately downstream of the TapP promoter it is important to either use direct repeats which do not contain an ATG codon therein or to eliminate any possible ATG start codon from the direct repeat sequence (using site specific mutation) such that transcription starts from the T7 polymerase ATG.

In the next step plant IV is crossed with plant III which does not express any of its exogenes, to yield a plant including a chromosome pair which is made up of a chromosome from plant III and a chromosome of plant IV. The resultant plant (V) is male sterile because the T7 polymerase produced in tapetal cells from chromosome A̲ binds the T7 promoter region on chromosome A and drives the expression of the toxin which leads to the degeneration of the tapetal cells and to male sterility.

This plant serves as the maternal plant for subsequent hybrid crosses (VII) in which the pollen of a compatible non-transgenic male fertile plant (VI) is used to fertilize plant V to yield (from plant V) fertile offsprings. This is achieved because of the 100% segregation of chromosomes A and A̲. The seeds collected from plant V are hybrid seeds which include either cassette VIIa or cassette VIIb.

It will be appreciated that the specific arrangement of the genes, recombination sites and promoters in cassette I can be altered and yet produce very similar results. For example the TapP promoter can be linked to the T7 polymerase and both flanked by the Lox sites. In this case the T7 promoter can be separated from the toxin gene by the TapP promoter and the T7 polymerase. Following excision the toxin is brought under the control of the T7 promoter.

Example 2

Figure 2:
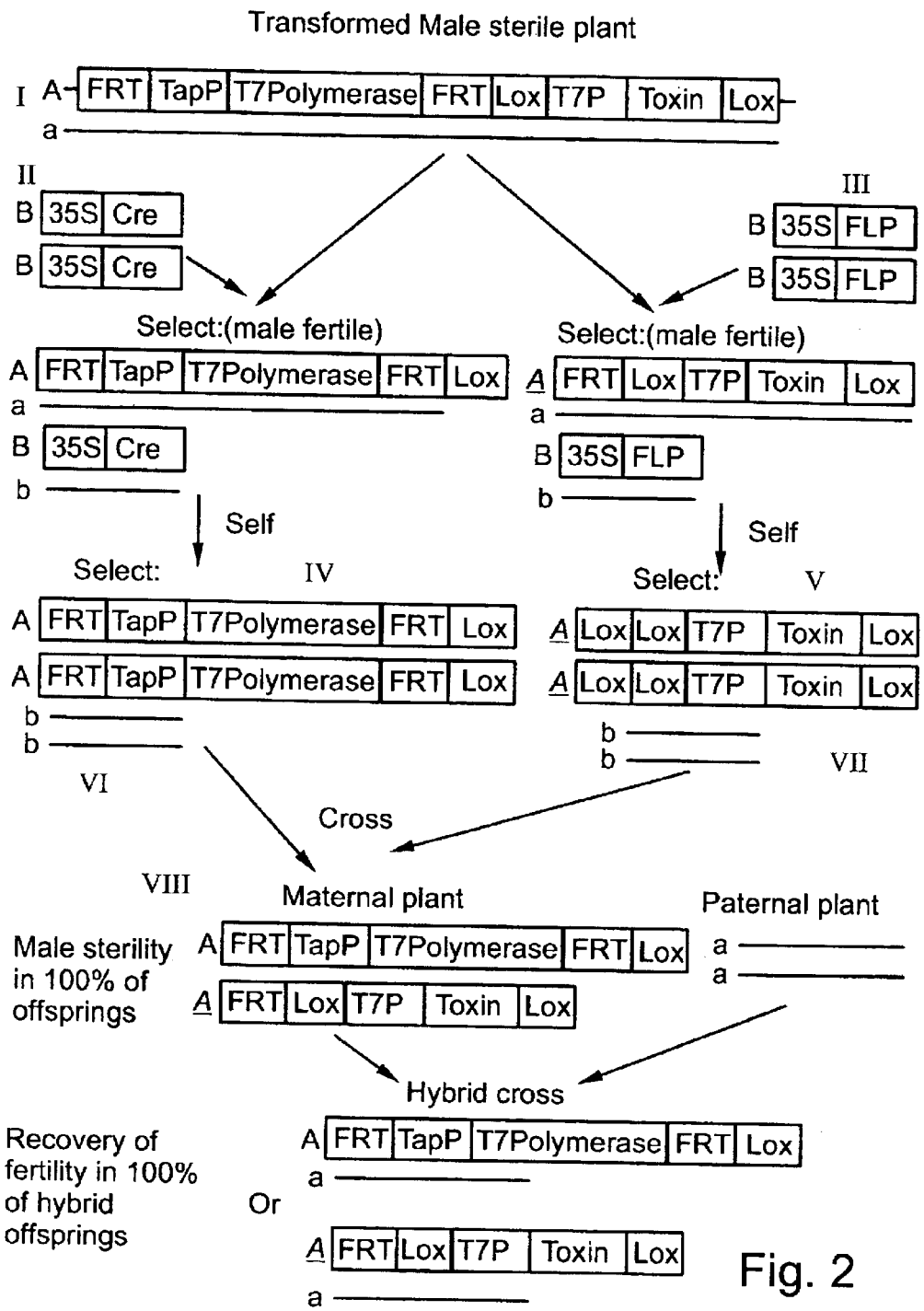
FIG. 2 is a flow diagram outlining another method for generating plants according to the teachings of the present invention. TapP—tapetum promoter; Lox—Cre recombinase recognition site; T7P—bacteriophage T7 promoter; T7 polymerase—the bacteriophage RNA polymerase recognizes the T7 promoter site; 35S—the CaMV promoter; CRE—the CRE recombinase; FRT—the FLP recombinase recognition site.

An alternative method for generating allelism is shown in FIG. 2. Again this method is shown with specific reference to induced male sterility, it is to be understood however that his method can be applied to generate allelism for any purpose.

FIG. 2 outlines another method for generating reversible male sterile plants according to the teachings of the present invention.

Plant tissue is transformed with cassette I and transgenic tissue is regenerated into identical transgenic plants. These transgenic plants are male sterile because they express both the T7 polymerase and as a result the toxin expressed from the T7 promoter According to this method cassette I includes a T7 polymerase operatively linked to the TapP promoter such as, for example, ant32, both flanked by the FRT recombinase sites. Cassette I further includes a toxin gene operatively linked to a T7 promoter, both flanked by the Lox sites.

Identical plants harboring cassette I are pollinated by a Cre recombinase plant (II) (homozygous for Cre) and an FLP recombinase plant (III) (homozygous for FLP). The resultant plants (IV and V) which contain either one of the gene and linked promoter are male fertile. As such these plants are selfed in order to lose the recombinase gene and to establish homozygotes of their recassettes (VI and VII). Plants VI and VII are crossed and the generated male sterile plant includes the two exogenes (T7 polymerase and the Toxin) in an allelic relationship. From this point on production of hybrid male fertile plants follows that described in Example 1.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

What is claimed is:

1. A method of generating a male sterile plant, the method comprising the steps of:
    (a) providing a first plant and a second plant each comprising an expression cassette in the same chromosomal location, said expression cassette comprising:
        (i) a first segment comprising a first transcribable polynucleotide sequence, said first transcribable polynucleotide sequence being operatively linked to a first promoter sequence, wherein said first segment is flanked by first site-specific recombination sequences; and
        (ii) a second segment, being linked to said first segment, said second segment comprising a second transcribable polynucleotide sequence, said second transcribable polynucleotide sequence being operatively linked to a second promoter sequence, wherein said second segment is flanked by second site-specific recombination sequences;
    (b) introducing by transformation or crossing a first polynucleotide sequence encoding a first recombinase into said first plant, wherein said first recombinase recognizes the first site-specific recombination sequences so as to excise said first segment and produce a first plant comprising the first recombinase, selfing said first plant comprising the first recombinase, and selecting a progeny devoid of the first polynucleotide sequence encoding said first recombinase, wherein the progeny comprises the second segment of the expression cassette but not the first segment;
    (c) introducing by transformation or crossing a second polynucleotide sequence encoding a second recombinase into said second plant, wherein said second recombinase recognizes the second site-specific recombination sequences so as to excise said second segment and produce a second plant comprising the second recombinase, selfing said second plant comprising the second recombinase, and selecting a progeny devoid of the second polynucleotide sequence encoding said second recombinase, wherein the progeny comprises the first segment of the expression cassette but not the second segment; and
    (d) crossing the progeny resulting from step (b) with the progeny resulting from step (c), so as to generate an offspring plant characterized by exogenic allelism, wherein expression of the first and the second transcribable polynucleotide sequences results in male sterility of the plant.

2. The method of claim 1, wherein the first transcribable polynucleotide sequence encodes a cytotoxic polypeptide or a cytostatic polypeptide.

3. The method of claim 2, wherein the cytostatic or cytotoxic polypeptide is pectate lyase, 1-3 β-glucanase, avidin, streptavidin, diphtheria toxin A-chain, URF13, indole acetic acid-lysine synthetase, cytA toxin, RNase-TI or Barnase.

4. The method of claim 1, wherein the first transcribable polynucleotide sequence encodes an antisense RNA molecule.

5. The method of claim 1, wherein the second transcribable polynucleotide sequence encodes an expression product that transactivates the expression of the first transcribable polynucleotide sequence.

6. The method of claim 5, wherein the expression product is a bacterial RNA polymerase or a bacteriophage RNA polymerase.

7. The method of claim 1, wherein the second promoter sequence is selected from the group consisting of constitutive promoters and induced promoters.

8. The method of claim 1, wherein the second promoter sequence is a tissue specific promoter.

9. A plant or plant seed produced according to the method of claim 1, wherein the plant or the plant seed is characterized by exogenic allelism, and by a genome that lacks a polynucleotide sequence encoding an exogenic recombinase.

10. A male sterile plant heterozygous for an expression cassette comprising:
    (a) a first segment comprising a first transcribable polynucleotide sequence, said first transcribable polynucleotide sequence being operatively linked to a first promoter sequence, wherein said first segment is flanked by first site-specific recombination sequences; and
    (b) a second segment, being linked to said first segment, said second segment comprising a second transcribable polynucleotide sequence, said second transcribable polynucleotide sequence being operatively linked to a second promoter sequence, wherein said second segment is flanked by second site-specific recombination sequences, and wherein said second transcribable polynucleotide sequence encodes a polypeptide or an RNA molecule that regulates the expression level of a product of said first transcribable polynucleotide sequence,
    wherein expression of the first and the second transcribable polynucleotide sequences results in male sterility of the plant.

* * * * *

UNITED STATES PATENT AND TRADEMARK OFFICE
CERTIFICATE OF CORRECTION

PATENT NO.   : 6,852,911 B1
DATED        : February 8, 2005
INVENTOR(S)  : Izhar It is certified that error appears in the above-identified patent and that said Letters Patent is hereby corrected as shown below:

Title page,
Item [73], Assignee, change "Fertiseed Ltd., Sitrya (IR)" to -- Fertiseeds Ltd., Ness-Ziona (IL) --.

Drawings,
Sheet 2, Fig. 2, step V, rows 1 and 2, change the first occurrence of "Lox" to -- FRT --.

Column 16,
Line 36, change "(1992 XXX)" to -- (1992) --.

Column 29,
Line 7, change each occurrence of "LOX" and -- Lox --.

Column 21,
Line 4, change "his" to -- this --.

Column 22,
Line 25, change "cytA" to -- CytA --.

Signed and Sealed this

Twenty-second Day of November, 2005

JON W. DUDAS
*Director of the United States Patent and Trademark Office*